United States Patent [19]
Tagamolila et al.

[11] Patent Number: 5,220,103
[45] Date of Patent: Jun. 15, 1993

[54] PROCESS FOR THE PREPARATION OF A CUMENE FEED FOR CUMENE OXIDATION

[75] Inventors: Constante P. Tagamolila, Arlington Heights; Russell C. Schulz, Darien, both of Ill.

[73] Assignee: UOP, Des Plaines, Ill.

[21] Appl. No.: 895,509

[22] Filed: Jun. 8, 1992

Related U.S. Application Data

[63] Continuation-in-part of Ser. No. 583,426, Sep. 17, 1990, Pat. No. 5,120,902.

[51] Int. Cl.$^5$ ............................................... C07C 7/10
[52] U.S. Cl. ................................. 585/836; 585/854; 585/868
[58] Field of Search .................. 585/836, 854, 868

[56] References Cited

U.S. PATENT DOCUMENTS

| | | | |
|---|---|---|---|
| 2,884,377 | 4/1959 | Bozich et al. | 583/854 |
| 3,284,506 | 11/1966 | Mantegazza et al. | 585/854 |
| 4,370,205 | 1/1983 | Pujado et al. | 585/804 |

Primary Examiner—Patrick P. Garvin
Assistant Examiner—E. D. Irzinski
Attorney, Agent, or Firm—Thomas K. McBride; John G. Tolomei; John G. Cutts, Jr.

[57] ABSTRACT

A process for the continuous preparation of a cumene feed for cumene oxidation from a fresh cumene stream and a recycle cumene stream containing trace quantities of at least one organic acid compound by a dilute caustic wash of the contaminated cumene streams followed by a water wash of the cumene streams in a single vessel with multiple contacting sections. A portion of the water wash is supplied by a waste water stream from an oxidate wash zone having trace quantities of cumene hydroperoxide.

7 Claims, 1 Drawing Sheet

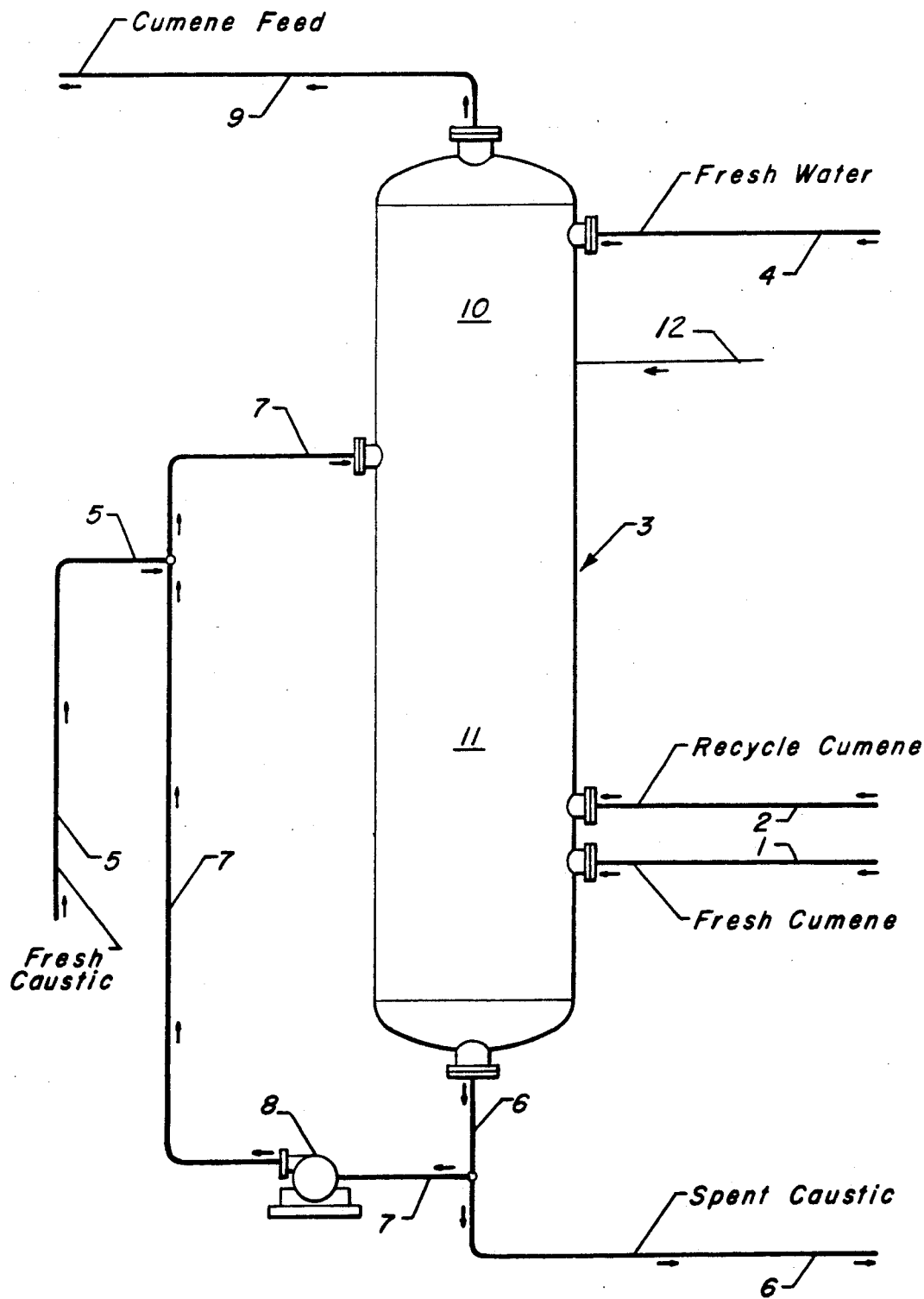

PROCESS FOR THE PREPARATION OF A CUMENE FEED FOR CUMENE OXIDATION

CROSS REFERENCE TO RELATED APPLICATION

The present application is a continuation-in-part of application Ser. No. 07/583,426 filed on Sep. 17, 1990, and now U.S. Pat. No. 5,120,902 all of which is incorporated by reference.

BACKGROUND OF THE INVENTION

The field of art to which this invention pertains is the preparation of a cumene feed for a cumene oxidation process. More specifically, the invention relates to a process for the preparation of a cumene feed for cumene oxidation from a fresh cumene stream and a recycle cumene stream containing trace quantities of at least one organic acid compound.

In general, phenols are prepared by the oxidation of a secondary alkylbenzene and the subsequent acid cleavage of the resulting alpha, alphadialkylbenzyl hydroperoxide to form a reaction mixture comprising a phenol, a ketone and unreacted secondary alkylbenzene. The acid cleavage is generally effected in the presence of an aqueous acid catalyst, usually sulfuric acid or sulfur dioxide in aqueous solution, or in the presence of an aqueous hydrochloric or perchloric acid solution. The present invention is particularly directed to a process wherein phenol is prepared by the air oxidation of cumene and the subsequent sulfuric acid cleavage of the resulting cumene hydroperoxide to form a reaction mixture comprising phenol, acetone and unreacted cumene. In addition to the principal products, there are formed varying amounts of by-products such as mesityl oxide, alpha-methylstryrene, p-cumylphenol, phenyldimethylcarbinol, acetophenone, and higher molecular weight phenols.

In the process of recovering phenol from the acid cleavage reaction mixture, the acidic reaction mixture is initially neutralized, either directly by the addition of caustic, or indirectly by contact with an ion exchange resin. In any case, the neutralized reaction mixture is fed to a distillation column, commonly referred to as a crude acetone column, at conditions to effect a crude separation of those materials boiling below phenol whereby an overhead fraction is recovered comprising substantially all of the acetone and lower boiling by-products, as well as a substantial portion of the water and unreacted cumene. Acetone is subsequently recovered, as is cumene, by the further distillation of the crude acetone column overhead. The resulting recovered cumene is recycled to the oxidation process.

The bottoms fraction recovered from the crude acetone column, comprising phenol and alpha-methylstyrene as well as the balance of the water and the bulk of the unreacted cumene, is typically treated for the separation of heavy ends and thereafter fed to a distillation column, commonly referred to as a cumene or alpha-methylstyrene column. The latter column is operated at conditions to separate an overhead fraction comprising water, cumene and alpha-methylstyrene from the higher boiling phenol product. The phenol, recovered as the bottoms fraction, further contains certain impurities, e.g., mesityl oxide and hydroxy acetone, and said impurities are treated and separated from this bottoms fraction to yield a substantially pure phenol product.

The overhead fraction from the cumene column will invariably comprise a significant amount of phenol, between 5 and 25 weight percent, as well as cumene and alpha-methylstyrene. It has been the practice to causticextract this overhead fraction and the cumene and the alpha-methylstyrene recovered as a water-immiscible organic phase is separated and recycled to oxidation as cumene. The phenol is recovered as sodium phenate in the aqueous phase, a practice which has necessitated a separate phenol recovery facility wherein the aqueous sodium phenate solution is acid treated and the resulting sprung phenol being recycled and combined with the acid cleavage product for recovery as hereinabove described, and the acidifying agent being subsequently extracted with a solvent or stripped with stream for economical recovery with phenol, followed by necessary treatment for safe disposal.

The total charge to the oxidation section of a phenol process unit consists of fresh cumene and recycle cumene from other various sections of the unit, i.e., from the spent air treating section, from the concentration section and from the fractionation section. The recycle cumene from the fractionation section normally would have undergone a caustic wash with a 5–30 weight percent caustic solution for the purpose of extracting the phenol and would be basic in nature due to the entrained caustic solution. The cumene recovered from the spent air and from the concentration sections, however, contains small quantities of organic acid compounds which are undesirable in the phenol process unit.

It is therefore necessary to caustic wash the recycle streams and is also desirable to wash the fresh cumene charged to the oxidizer with at least a dilute caustic solution. It is also important that a water wash be performed after the caustic wash in order to remove the entrained caustic since a breakthrough of the caustic to the decomposer would neutralize the small quantity of acid catalyst in the decomposer.

The prior art teaches that the caustic wash and the water wash may be performed in a complex manner and those skilled in the prior art have sought a more efficient process to prepare a cumene feed for cumene oxidation. We have discovered a process for achieving this result which is less complex, more economical and more space efficient.

Previously, it was also advantageous to caustic wash and water wash the oxidizer effluent to remove traces of organic acids, i.e., formic acid, that are formed in the oxidation reaction in order to prevent corrosion in the downstream sections, especially in the fractionation section. In the prior art processes, the waste aqueous phase is normally sent to a cumene extraction column where the cumene hydroperoxide is extracted from the aqueous phase by using a slipstream of the fresh cumene charge which is then sent to the oxidizer. In accordance with the present invention this waste aqueous phase, referred to hereinafter as oxidate wash, is introduced into the countercurrent contacting zone to provide water and to recover trace quantities of cumene hydroperoxide. This eliminates the need for the cumene extraction column and the concomitant expense.

In accordance with the present invention, the total feed caustic and water wash and/or the cumene extraction column is replaced by a single contacter tower as described hereinafter. This single contacter tower is successfully used for both achieving the caustic washing and the subsequent water washing. A process for the preparation of a cumene feed, sufficiently free of phenol, acids and caustic for cumene oxidation which is less complex, more economical and space efficient is disclosed.

BRIEF SUMMARY OF THE INVENTION

The invention provides a process for the preparation of a cumene feed for cumene oxidation from a fresh cumene stream and a recycle cumene stream containing trace quantities of at least one organic acid compound by means of introducing the fresh cumene stream and the recycle cumene stream containing trace quantities of an organic acid compound into a lower zone of a generally vertical elongated countercurrent contacting zone having a caustic/hydrocarbon contacting section in a lower portion of the countercurrent contacting zone and a water/hydrocarbon contacting section in an upper portion of the countercurrent contacting zone; introducing a fresh water stream to provide water to the water/hydrocarbon contacting section; introducing a waste water stream from an oxidate wash to provide water to the water/hydrocarbon contacting section and to recover trace quantities of cumene hydroperoxide contained in the waste water stream; introducing an aqueous caustic scrubbing solution to provide caustic solution to the caustic/hydrocarbon contacting section; removing spent aqueous caustic solution from the countercurrent contacting zone; and removing and recovering a cumene feed from the countercurrent contacting zone. Important elements of the improved process are less complex equipment requirements, more economical operation and more efficient use of plot space. In accordance with the present invention, the total feed caustic wash and the cumene extraction column found in the prior art processes may be advantageously replaced by a single contacting tower as described herein.

One embodiment of the present invention may be characterized as a process for the preparation of a cumene feed for cumene oxidation from a fresh cumene stream and a recycle cumene stream containing trace quantities of at least one organic acid compound which process comprises: (a) introducing the fresh cumene stream and the recycle cumene stream containing trace quantities of at least one organic acid compound into an intermediate, lower locus of a generally vertical, elongated, countercurrent contacting zone having a caustic/hydrocarbon contacting section in a lower portion of the countercurrent contacting zone and a water/hydrocarbon contacting section in an upper portion of the countercurrent contacting zone; (b) introducing a fresh water stream into an intermediate, upper locus of the countercurrent contacting zone at the top of the water/hydrocarbon contacting section to provide water to the water/hydrocarbon contacting section; (c) introducing a waste water stream from an oxidate wash having trace quantities of cumene hydroperoxide into an intermediate upper locus of said countercurrent contacting zone at the top of said water/hydrocarbon contacting section to provide water to the water/hydrocarbon contacting section and to recover trace quantities of cumene hydroperoxide contained in the waste water stream; (d) introducing an aqueous caustic scrubbing solution into an intermediate locus of the countercurrent contacting zone at the top of the caustic/hydrocarbon contacting section to provide caustic solution to the caustic/hydrocarbon contacting section; (e) removing spent aqueous caustic solution from the countercurrent contacting zone at a bottom locus of the countercurrent contacting zone at the bottom of the caustic/hydrocarbon contacting section; and (f) removing a cumene feed from the countercurrent contacting zone at an upper locus of the countercurrent contacting zone at the top of the water/hydrocarbon contacting section.

Another aspect of the invention is the staging of the hydrocarbon stream injection points, i.e., the fresh cumene and the recycle cumene from the fractionation section is preferably introduced at a location below the injection point of the other combined recycle streams, including recycle from the concentration section and recycle cumene from the spent air treatment decanter.

Cumene hydroperoxide (CHP) is somewhat soluble in caustic and the solubility increases with caustic concentration. The other combined recycle streams, including recycle from the concentration section and recycle cumene from the spent air treatment decanter, contain CHP, a portion of which is carried by the caustic wash on its downward path through the countercurrent contacting zone. By contacting the spent caustic with fresh cumene and the recycle stream from fractionation, both of which contain negligible amounts of CHP, the CHP in the flowing caustic waste stream is re-extracted and returned to the hydrocarbon phase which minimizes the loss of CHP and increases product yields.

Other embodiments of the present invention encompass further details such as preferred cumene feed streams, aqueous caustic scrubbing solutions and operating conditions, all of which are hereinafter disclosed in the following discussion of each of these facets of the invention.

BRIEF DESCRIPTION OF THE DRAWING

The drawing is a simplified process flow diagram of a preferred embodiment of the present invention.

DETAILED DESCRIPTION OF THE INVENTION

The overall process to which this invention pertains concerns the oxidation of a secondary alkylbenzene, for example, isopropylbenzene (cumene) isobutylbenzene, isoamylbenzene, 1-methyl-4-isopropylbenzene, p-diisopropylbenzene, p-diisobutylbenzene, 1-isopropyl-4-isobutylbenzene, cyclohexyl benzene, and the like, to form the corresponding hydroperoxide, i.e., isopropylbenzene hydroperoxide, isobutylbenzene hydroperoxide, isoamylbenzene hydroperoxide, 1-methyl-4-isopropylbenzene hydroperoxide, p-diisopropylbenzene hydroperoxide, p-diisobutylbenzene hydroperoxide, 1-isobutyl-4-isopropylbenzene dihydroperoxide, cyclohexylbenzene hydroperoxide, and the like. The present invention is particularly directed to a process for the preparation of a cumene feed for cumene oxidation from a fresh cumene stream and a recycle cumene stream containing trace quantities of at least one organic acid compound. The organic acid compound is selected from the group consisting of formic acid, acetic acid, benzoic acid, propionic acid and butyric acid.

The aforesaid oxidation reaction is effected at conditions well known in the art. The hydroperoxide oxidation product can be prepared by direct liquid phase oxidation of the selected alkybenzene with oxygen, or an oxygencontaining gas such as air, usually at an elevated temperature. The oxidation reaction proceeds slowly through an initial induction period, accelerating to a more favorable rate with the formation of the hydroperoxide which exerts a catalytic effect on the oxidation reaction. This initial induction period is eliminated, or substantially reduced, by initially including a hydroperoxide in the reaction mixture, usually the hydroperoxide product of the reaction. However, other materials are disclosed in the art which exhibit a similar catalytic effect. Temperatures effecting the oxidation reaction range from about room temperature to about the boiling point of the hydrocarbon subjected to oxidation, which, in the case of cumene, is about 305° F. In general, it is preferred to utilize an elevated temperature in the range of from about 120° to about 265° F. The optimum temperature will depend on the particular alkylbenzene to be oxidized and on the reaction conditions otherwise employed. The oxidation can be effected at pressures ranging from about atmospheric to about 500 psig, although a pressure not exceeding about 90 psig is generally preferred. It is desirable to limit the contact time of the reactants at oxidation conditions to effect substantially less than complete conversion of the alkylbenzene to the corresponding hydroperoxide. For example, in the oxidation of cumene, it is desirable to limit the contact time of the cumene and the oxidizing agent so that the concentration of the resulting cumene hydroperoxide does not exceed about 40 wt. %.

In accordance with the present invention, the effluent from the oxidation reaction section is caustic washed and water washed to remove trace organic acids, such as, formic acid, that are formed in the oxidation reaction in order to prevent corrosion in the downstream sections, especially in the fractionation section. The waste water from this wash is conveniently utilized by further treatment and use in the hereinafter described countercurrent contacting zone.

The vertical, countercurrent contacting zone of the present invention has a caustic/hydrocarbon contacting section in a lower portion of the countercurrent contacting zone and a water/hydrocarbon contacting section in an upper portion of the countercurrent contacting zone. The caustic/hydrocarbon section is where a downwardly flowing caustic solution is countercurrently contacted with an upwardly flowing hydrocarbon stream to remove trace quantities of organic acid and any residual phenol which may not have been removed from upstream treatment of the recycled hydrocarbon stream from the hydrocarbon stream. The water/hydrocarbon contacting section is where a downwardly flowing fresh water stream is countercurrently contacted with an upwardly flowing hydrocarbon stream to remove dissolved and entrained caustic solution from the hydrocarbon stream. The fresh cumene and recycle cumene are introduced at or near the bottom of the countercurrent contacting zone and a relatively clean cumene stream is removed from the top of the countercurrent contacting zone. A spent caustic stream is removed from the bottom of the countercurrent contacting zone and another caustic stream is optionally circulated from the bottom of the countercurrent contacting zone and introduced at the top of the water/hydrocarbon contacting section together with fresh caustic. Fresh water is introduced at or near the top of the countercurrent contacting zone which is also the top of the water/hydrocarbon contacting stream. The fresh water flowing down the caustic/hydrocarbon contacting section provides the diluent required for the dilution of the make-up caustic injection. In addition to the fresh water, according to the present invention, a waste water stream from an oxidation wash is used to supplement the fresh water. The waste water from the oxidate wash preferably comprises from about 5 to about 90 volume percent of the total water introduced into the water/hydrocarbon contacting section.

In accordance with the present invention, the vertical, countercurrent contacting zone is preferably contained in a vessel which has packing, trays or other convenient means to provide countercurrent liquid-liquid extraction. The contacting zone is preferably operated at a pressure from about atmospheric (0 kPa gauge) to about 150 psig (1035 kPa gauge) and a temperature from about 41° F. (5° C.) to about 140° F. (60° C.). Any convenient operating temperature and pressure may be used in the practice of the present invention.

In the water/hydrocarbon contacting zone the volumetric ratio of water to hydrocarbon may range from about 1:100 to about 20:100, and in the caustic/hydrocarbon contacting zone the volumetric ratio of aqueous caustic solution to hydrocarbon may range from about 1:100 to about 20:100.

The aqueous caustic solution which is introduced into the caustic/hydrocarbon contacting zone preferably contains from about 0.1 to about 5 weight percent caustic and the preferred caustic solution is an aqueous sodium hydroxide solution. Make-up caustic solutions may have concentrations from about 5 to about 50 weight percent caustic.

The further description of the process of this invention is presented with reference to the attached drawing. The drawing is a simplified flow diagram of a preferred embodiment of this invention and is not intended as an undue limitation on the generally broad scope of the invention as set out in the appended claims. Certain hardware such as valves, pumps, compressors, heat exchangers, instrumentation and controls, have been omitted as not essential to a clear understanding of the invention. The use and application of this hardware is well within the skill of the art.

Referring now to the drawing, a fresh cumene stream and caustic washed recycle stream from a fractionation section in an amount of 33,500 pounds per hour and containing 10 weight ppm phenol is introduced via conduit 1 into countercurrent contacting vessel 3. Combined recycle cumene streams consisting of cumene recovered from spent air and from a concentration section in an amount of 91,406 pounds per hour and containing three weight percent cumene hydroperoxide, 50 weight ppm phenol and trace amounts of organic acid are introduced via conduit 2 into countercurrent contacting vessel 3. These two combined streams of cumene upon entering countercurrent contacting vessel 3 begin to flow in a generally upward manner through caustic/hydrocarbon contacting zone 11 and are contacted with a generally downwardly flowing aqueous caustic stream in a countercurrent manner in order to extract organic acid compounds and trace quantities of phenol which are introduced with the cumene streams. The upwardly flowing cumene then enters a water/hydrocarbon contacting zone 10 wherein the cumene is countercurrently contacted with a waste water stream in an amount of 500 pounds per hour from an oxidate wash which is introduced into countercurrent contacting vessel 3 via conduit 12 and subsequently with fresh water which is introduced into countercurrent contacting vessel 3 via conduit 4. The fresh water entering via conduit 4 is in an amount of 2,000 pounds per hour and is utilized to remove entrained caustic and to ensure a cumene feed stream which is essentially free of entrained aqueous caustic. A resulting cumene feed stream is removed from countercurrent contacting vessel 3 via conduit 9 in an amount of 91,400 pounds per hour. This resulting cumene feed may then be coalesced to remove entrained water before it is introduced into oxidizers to produce cumene hydroperoxide. An aqueous caustic solution containing about 1 weight percent sodium hydroxide is removed from the bottom of the countercurrent contacting vessel 3 via conduit 6. At least a portion of this aqueous caustic stream is recirculated via conduit 7 and pump 8 to provide an aqueous caustic solution for caustic/hydrocarbon contacting zone 11. The net caustic solution removed via conduit 6 from countercurrent contacting vessel 3 is removed from the process and recovered for safe disposal. A fresh aqueous caustic make-up stream in an amount of 82 pounds per hour and containing 27 weight percent sodium hydroxide is introduced into the process via conduit 5 and is then introduced into countercurrent contacting vessel 3 via conduit 7.

The foregoing description and drawing clearly illustrate the advantages encompassed by the process of the present invention and the benefits to be afforded with the use thereof.

What is claimed is:

1. A process for the preparation of a cumene feed for cumene oxidation from a fresh cumene stream and a recycle cumene stream containing trace quantities of at least one organic acid compound which process comprises:
   (a) introducing said fresh cumene stream and said recycle cumene stream containing trace quantities of at least one organic acid compound into an intermediate, lower locus of a generally vertical, elongated, countercurrent contacting zone having a caustic/hydrocarbon contacting section in a lower portion of said countercurrent contacting zone and a water/hydrocarbon contacting section in an upper portion of said countercurrent contacting zone;
   (b) introducing a fresh water stream into an intermediate, upper locus of said countercurrent contacting zone at the top of said water/hydrocarbon contacting section to provide water to said water/hydrocarbon contacting section;
   (c) introducing a waste water stream having trace quantities of cumene hydroperoxide resulting from the water wash of a cumene oxidation effluent stream into an intermediate, upper locus of said countercurrent contacting zone at the top of said water/hydrocarbon contacting section to provide water to said water/hydrocarbon contacting section and to recover trace quantities of cumene hydroperoxide contained in said waste water stream;
   (d) introducing an aqueous caustic scrubbing solution into an intermediate locus of said countercurrent contacting zone at the top of said caustic/hydrocarbon contacting section to provide caustic solution to said caustic/hydrocarbon contacting section;
   (e) removing spent aqueous caustic solution from said countercurrent contacting zone at a bottom locus of said countercurrent contacting zone at the bottom of said caustic/hydrocarbon contacting section; and
   (f) removing a cumene feed from said countercurrent contacting zone at an upper locus of said countercurrent contacting zone at the top of said water/hydrocarbon contacting section.

2. The process of claim 1 wherein said organic acid compound is selected from the group consisting of formic acid, acetic acid, benzoic acid, propionic acid and butyric acid.

3. The process of claim 1 wherein said generally vertical, elongated countercurrent contacting zone is operated at a pressure from about atmospheric (0 kPa gauge) to about 150 psig (1035 kPa gauge) and a temperature from about 41° F. (5° C.) to about 140° F. (60° C.).

4. The process of claim 1 wherein said water/hydrocarbon contacting zone is operated with a water to hydrocarbon volumetric ratio from about 1:100 to about 20:100.

5. The process of claim 1 wherein said caustic/hydrocarbon contacting zone is operated with an aqueous caustic solution to hydrocarbon volumetric ratio from about 1:100 to about 20:100.

6. The process of claim 1 wherein said aqueous caustic scrubbing solution contains sodium hydroxide.

7. The process of claim 1 wherein said waste water stream from said oxidate wash comprises from about 10 to about 90 volume percent of the total water introduced into said water/hydrocarbon contacting section.

* * * * *